United States Patent [19]

Lindsey

[11] Patent Number: 4,671,273
[45] Date of Patent: Jun. 9, 1987

[54] LASER HAND PIECE, FOR USE IN OPTHALMIC, PLASTIC, AND EAR, NOSE, AND THROAT SURGERY

[76] Inventor: Ernest J. Lindsey, 4632 Call Rd., Mt. Sterling, Ohio 43143

[21] Appl. No.: 591,296

[22] Filed: Mar. 19, 1984

[51] Int. Cl.$^4$ ............................................. A61B 17/36
[52] U.S. Cl. ................. 128/303.1; 128/398; 219/121 LR; 350/96.18; 350/96.20
[58] Field of Search ............... 128/303.1, 395–398, 128/303.13; 219/121 LR, 121 LV; 350/96.18, 96.20

[56] References Cited

U.S. PATENT DOCUMENTS

| | | | |
|---|---|---|---|
| 3,382,343 | 5/1968 | Muncheryan | 219/121 LR |
| 3,383,491 | 5/1968 | Muncheryan | 219/121 LR |
| 3,467,098 | 9/1969 | Ayres | 128/303.1 |
| 3,821,510 | 6/1974 | Muncheryan | 128/303.1 X |
| 3,834,391 | 9/1974 | Block | 128/303.1 |
| 3,843,865 | 10/1974 | Nath | 128/395 X |
| 3,865,113 | 2/1975 | Sharon et al. | 128/303.1 |
| 4,076,028 | 2/1978 | Simmons | 128/303.13 |
| 4,538,609 | 9/1985 | Takenaka et al. | 128/395 |

FOREIGN PATENT DOCUMENTS

| | | | |
|---|---|---|---|
| 0069351 | 1/1983 | European Pat. Off. | 128/303.1 |
| 2513109 | 3/1983 | France | 128/303.1 |

OTHER PUBLICATIONS

Smith et al., "New Trends . . . Microsurgery", Proc. Soc. Photo., Opt. Inst., 1980, pp. 173–182.

Primary Examiner—Lee S. Cohen
Attorney, Agent, or Firm—John L. Gray

[57] ABSTRACT

A hand held unit connected to a laser source by means of fiber optics which may be used in dermatology by conveying the laser light at the proper selected intensity to the skin area to be treated. The unit, with a detachable probe attached, may be used for a variety of intraocular applications in ophthalmic surgery, and may be used for ear, nose, and throat surgery with or without the detachable probe attached.

8 Claims, 2 Drawing Figures

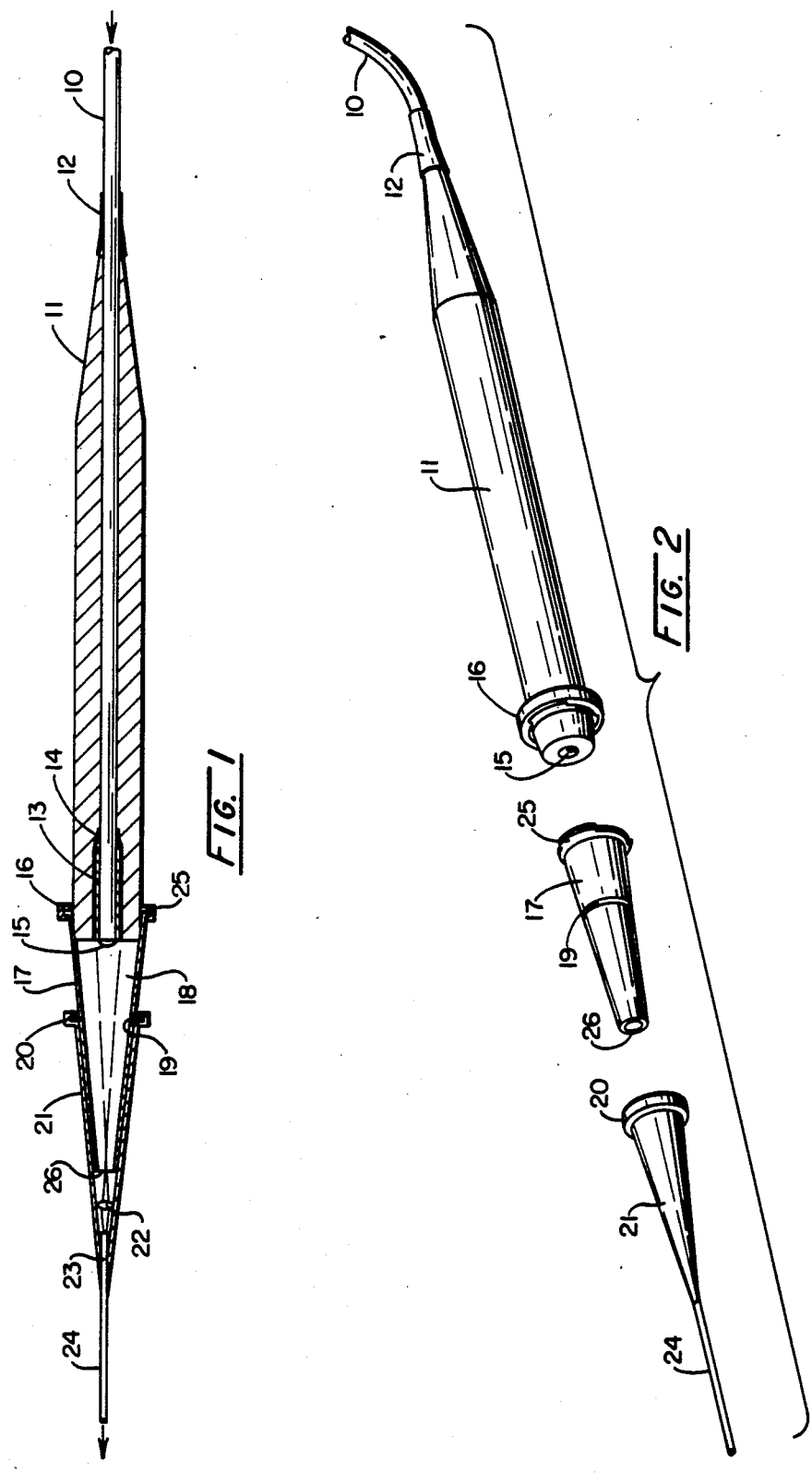

LASER HAND PIECE, FOR USE IN OPTHALMIC, PLASTIC, AND EAR, NOSE, AND THROAT SURGERY

BACKGROUND OF THE INVENTION

With the advent of laser technology being used in connection with surgery, the application of the laser to a wide variety of surgical procedures has evolved.

By strategically placing the laser adjacent to a number of different operating rooms within a maximum distance of approximately 65 feet, and the use of a fiber optic cord, the same laser may be used for entirely different types of surgery, requiring different surgical procedures and set-ups, and necessitating different types of operating room facilities.

The present state of the art utilizes hand held units for each type of surgery for which the laser source is used. Since oftentimes these units cannot be autoclaved and must be disposed of following the surgical procedure, this increases the cost of the use of the laser considerably.

SUMMARY OF THE INVENTION

The invention of applicant is a hand held unit for laser radiation application, which may be used for a variety of different surgical procedures. It may be autoclaved or, optionally, a portion of it may be disposed of at minimal cost.

This invention, therefore, has as one object to provide a hand held unit which may be used in conjunction with a fiber optics cord from a laser for a variety of different surgical procedures.

It is a further object of this invention to provide such a hand held unit which is provided with a detachable portion which either may be designed for disposal after a single use, having been sterilized when produced, or which may be designed for autoclaving, if appropriate.

It is a further object of this invention to provide such a hand held unit which is easy to use and which may be used for ophthalmic surgery, dermatology, or ear, nose, and throat surgery.

These, together with other objectives and advantages of the invention, should become apparent in the details of construction and operation, as more fully described herein and claimed, reference being had to the accompanying drawings forming a part hereof wherein like numerals refer to like parts throughout.

BRIEF DESCRIPTION OF THE DRAWINGS

FIG. 1 is a sectional view of the invention as assembled with all of the components in place.

FIG. 2 is a perspective view of the invention with the components separated.

DETAILED DESCRIPTION OF THE INVENTION

Referring more particularly now to FIG. 1, 10 is a fiber optics cord which preferably is about three feet in length and which may be attached by means of a conventional twist lock fitting (not shown) to a fiber optics cord from a laser, such as an argon laser (not shown). Cord 10 is positioned within trunk 11 and is held firmly thereto by means of electronic shrink tubing 12. The inner end of cord 10 is held within metal sleeve 13 by means of electronic shrink tubing 14. The end of cord 10 terminates in lens 15 which preferably is 3.5 millimeters in diameter.

Trunk 11 is provided the female portion of a bayonet fitting 16 near the end adjacent lens 15. The corresponding male bayonet portion is better shown in FIG. 2 and will be described thereunder. Conical member 17 is adapted to fit over the end of trunk 11 and may be provided with a reflective coating 18 on the interior surface thereof, in order to absorb light and dissipate heat. Conical member 17 is provided with a circumferentially extending ridge 19 which is adapted to receive the end 20 of probe 21 as a snap fitting. Probe 21 is provided with a plastic lens 22 which is connected to fiber optics 23 positioned in metal probe 24. The geometry of the lenses is such that the argon laser light emitted from the end of probe 24 is approximately a 50 micron spot.

Referring now more particularly to FIG. 2, it will be seen that conical member 17 may readily be detached from trunk 11 merely by twisting it and removing it therefrom. FIG. 2 particularly shows the male member 25 of the bayonet fitting on conical member 17 which is adapted to engage the female bayonet portion 16 on trunk 11. Likewise, probe 21 is provided with end 20 to engage circumferential extending ridge 19 to produce a snap fit when attached thereto.

In using this invention for dermatology, the probe 21 is not attached to conical member 17. Conical member 17 is attached by means of the bayonet fittings 25 and 16 to trunk 11. The lens 15 is so designed in combination with the length of conical member 17 so as to produce a focal point of laser light at the opening 26 of conical member 17. By holding this member away from the skin being treated, a more diffuse, lower energy, laser treatment may be obtained.

By using this device in dermatology, removal of skin lesions, cholestomy from the inner ear, and keloids from ear lobes may be accomplished. Coagulation of blood vessels, and other forms of skin surgery may also be performed. In some cases it may be desirable in ear, nose, and throat surgery to utilize the probe 21 attached to conical member 17.

With the probe 21 attached to conical member 17, the unit may be used for a variety of ophthalmic applications. These include an intraocular light source in vitrectomy surgery and as an intraocular laser in vitrectomy surgery. It may also be used for coagulation of intraocular blood vessels in vitrectomy surgery and for the removal of muscles in vitrectomy surgery. It may also be used for retinal detachment surgery and for eye muscle surgery, as well as pan retinal procedures and irridotomy in cataract surgery.

In retinal detachment surgery, the hand piece enables the surgeon to laser closer to the macula on the retina. Because the device may be disassembled into three sections, it is adaptable to having portions thereof sterile when produced and disposable, or if desired, all or some of the portions of the hand piece may be autoclaved for sterility between uses.

While this invention has been described in its preferred embodiment, it is appreciated that variations thereon may be made without departing from the scope and spirit of the invention.

What is claimed is:

1. A hand held unit for use in surgery utilizing coherent radiation comprising a first fiber optic cord, one end of which is capable of being connected to a second fiber optic cord from a source of coherent radiation, a hollow cylindrical probe of a size adatped to be readily held by one hand, said first fiber optic cord being positioned within said hollow cylindrical probe and extending the length thereof, a focussing lens positioned within said probe at one end thereof, and the other end of said first fiber optic cord terminating in said lens, a hollow member in the shape of a frustum of a cone, removably attached to said hollow cylindrical probe at the base of said cone and coaxial therewith and adjacent to said focussing lens, said hollow conical frustrum-shaped member being of a length to permit the coherent radiation passing through said focussing lens to reach a focal point at the smaller opening of said conical frustum-shaped member, and being provided with means on the smaller end thereof to permit the attachment on the smaller end thereof of a hollow conical member for transmitting the coherent radiation to a surgical area.

2. The hand held unit of claim 1, wherein said hollow member in the shape of a frustum of a cone is provided with a mirror coating on the inside surface thereof.

3. The hand held unit at claim 1 wherein said first fiber optic cord is held within said hollow cylindrical probe by means of electronic shrink tubing.

4. The hand held unit of claim 1 wherein said first fiber optic cord is positioned within a metal shaft adjacent said focussing lens.

5. The hand held unit of claim 1 wherein said hollow cylindrical probe is made of metal.

6. A hollow probe comprising a hollow conical member having a base capable of being removably attached to a hand held unit for use in surgery, a hollow rigid cylindrical member connected to the vertex of said conical member and coaxial therewith, a focussing lens in the interior of said conical member and adjacent the smaller end thereof and of a size and shape so as to be capable of gathering diffuse radiation and refocussing it into coherent radiation, and a fiber optic cord positioned within said hollow rigid cylindrical member so as to transmit said coherent radiation through said hollow rigid cylindrical member.

7. The hollow probe of claim 6 wherein said cylindrical member is metal.

8. A hand held unit for use in surgery utilizing coherent radiation comprising a first fiber optic cord, one end of which is capable of being connected to a second fiber optic cord from a source of coherent radiation, a hollow cylindrical probe of a size adapted to be readily held by one hand, said first fiber optic cord being positioned within said hollow cylindrical probe and extending the length thereof, a focussing lens positioned within said probe at one end thereof, and the other end of said first fiber optic cord terminating in said lens, a hollow member in the shape of a frustum of a cone, removably attached to said hollow cylindrical probe at the base of said cone and coaxial therewith and adjacent to said focussing lens, said hollow conical frustum-shaped member being of a length to permit the coherent radiation passing through said focussing lens to reach a focal point at the smaller opening of said conical frustum-shaped member, a hollow conical member-removably attached to the smaller end of said conical frustum-shaped member, said hollow conical member being removably attached to said conical frustum-shaped member at the base of said hollow conical member, said hollow conical member being coaxial with said conical frustum-shaped member, said hollow conical member having a hollow rigid cylindrical member connected to the vertex of said hollow conical member and being coaxial therewith, a focussing lens in the interior of said conical member and adjacent the smaller end thereof and a size and shape so as to be capable of gathering diffuse radiation and refocussing it into coherent radiation, and a fiber optic cord positioned within said hollow rigid cylindrical member so as to transmit said coherent radiation through said hollow rigid cylindrical member.

* * * * *

UNITED STATES PATENT AND TRADEMARK OFFICE
CERTIFICATE OF CORRECTION

PATENT NO. : 4,671,273
DATED : June 9, 1987
INVENTOR(S) : Ernest J. Lindsey

It is certified that error appears in the above-identified patent and that said Letters Patent are hereby corrected as shown below:

In the Title: The word "ophthalmic" has the first letter "h" omitted after the "p".

In the Detailed Description of the Invention: Column 2, line 3, the word "with" is omitted after "provided" and before "the".

In the Claims: Column 4, line 39, the word "of" is omitted after "and" and before "a".

Signed and Sealed this

Eighth Day of September, 1987

Attest:

DONALD J. QUIGG

*Attesting Officer*   *Commissioner of Patents and Trademarks*